United States Patent [19]
Bellinger

[11] Patent Number: 5,445,146
[45] Date of Patent: Aug. 29, 1995

[54] BIOLOGICAL TISSUE STIMULATION BY LOW LEVEL OPTICAL ENERGY

[76] Inventor: Gary J. Bellinger, 10670 N. Central Expressway Suite 405, Dallas, Tex. 75231

[21] Appl. No.: 724,335

[22] Filed: Jul. 1, 1991

[51] Int. Cl.⁶ ............................................. A61N 5/00
[52] U.S. Cl. ......................................... 607/89; 606/3
[58] Field of Search ....................... 128/395, 396, 397; 606/2, 3, 10, 11; 607/88, 89, 90; 604/20

[56] References Cited

U.S. PATENT DOCUMENTS

| | | | |
|---|---|---|---|
| 4,854,320 | 8/1989 | Dew et al. | 128/397 |
| 4,930,504 | 6/1990 | Diamantopolous et al. | 606/3 |
| 4,931,053 | 6/1990 | L'Esperance, Jr. | 128/395 |
| 4,966,144 | 10/1990 | Rochkind et al. | 128/395 |
| 5,002,051 | 3/1991 | Dew et al. | 128/395 |
| 5,161,526 | 11/1992 | Hellwing et al. | 606/3 |

*Primary Examiner*—Jessica J. Harrison
*Attorney, Agent, or Firm*—Timmons & Kelly; W. Thomas Timmons

[57] ABSTRACT

Biological tissue of a living subject is irradiated with optical energy at a wavelength and at a power dissipation level to cause the amount of optical energy absorbed and converted to heat in the tissue to be within a range bounded by a minimum absorption rate sufficient to elevate the average temperature of the irradiated tissue to a level above the basal body temperature, but which is less than the absorption rate at which tissue is converted into a collagenous substance. According to this method, a therapeutic, warming effect is produced within the irradiated tissue, but without causing tissue damage by thermal overheating. The method of using a low level reactive laser system from 100 milliwatts to 800 milliwatts in either a pulsed or continuous mode with optical energy produced by a Nd:YAG laser at a fundamental wavelength of 1064 nanometers has been found to reduce pain in soft tissues, reduce inflammation and enhance the healing of tissue by stimulation of microcirculation without subjecting the living tissue to damaging thermal effects. The energy density of the irradiated tissue is limited to the range of from about 1 joule per square centimeter to about 15 joules per square centimeter.

12 Claims, No Drawings

BIOLOGICAL TISSUE STIMULATION BY LOW LEVEL OPTICAL ENERGY

FIELD OF THE INVENTION

The present invention relates generally to the treatment of living biological tissue by optical irradiation, and in particular to a method for stimulating soft, living tissue by laser irradiation.

BACKGROUND OF THE INVENTION

Various non-surgical means have been employed in the therapeutic treatment of living tissue. Such techniques have included the application of ultrasonic energy, electrical stimulation, high frequency stimulation by diathermy, X-rays and microwave irradiation. Techniques such as electrical stimulation, diathermy, X-ray and microwave radiation have shown some therapeutic benefit for soft tissues. However, their use has been somewhat limited because of tissue damage caused by excessive thermal effects. Consequently, the energy levels associated with therapeutic treatments involving diathermy, X-ray, microwave and electrical stimulation have been limited to such low levels that little or no benefit has been obtained. Moreover, the dosage or exposure to microwaves and X-ray radiation must be carefully controlled to avoid radiation related health problems. Ultrasonic energy is non-preferentially absorbed and affects all of the surrounding tissue.

Optical energy generated by lasers has been applied for various medical and surgical purposes because of the monochromatic and coherent nature of laser light which can be selectively absorbed by living tissue depending upon certain characteristics of the wavelength of the light and properties of the irradiated tissue, including reflectivity, absorption coefficient, scattering coefficient, thermal conductivity and thermal diffusion constant. The reflectivity, absorption coefficient and scattering coefficient are dependent upon the wavelength of the optical radiation. The absorption coefficient is known to depend upon such factors as interband transition, free electron absorption, grid absorption (phonon absorption), and impurity absorption, which are dependent upon the wavelength of the optical radiation.

In living tissue, water is a predominant component which has an absorption band according to the vibration of water molecules in the infrared range. In the visible range, there exists absorption due to the presence of hemoglobin. Further, the scattering coefficient in living tissue is a dominant factor.

Thus, for a given tissue type, the laser light may propagate through the tissue, substantially unattenuated, or may be almost entirely absorbed. The extent to which the tissue is heated and ultimately destroyed depends on the extent to which it absorbs the optical energy. It is generally preferred that the laser light be essentially transmissive in tissues which are desired not to be affected, and absorbed by the tissues which are to be affected. For example, when applying laser radiation in a tissue field which is wet with blood or water, it is desired that the optical energy not be absorbed by the water or blood, thereby permitting the laser energy to be directed specifically to the tissue to be treated. Another advantage of laser treatment is that the optical energy can be delivered to the treatment tissues in a precise, well defined location and at predetermined, limited energy levels.

DESCRIPTION OF THE PRIOR ART

Ruby and argon lasers are known to emit optical energy in the visible portion of the electromagnetic spectrum, and have been used successfully in the field of ophthalmology to reattach retinas to the underlying choroidea and to treat glaucoma by perforating anterior portions of the eye to relieve interoccular pressure. The ruby laser energy has a wavelength of 694 nanometers and is in the red portion of the visible spectrum. The argon laser emits energy at 488 and 515 nanometers and thus appears in the blue-green portion of the visible spectrum. The ruby and argon laser beams are minimally absorbed by water, but are intensely absorbed by blood chromogen hemoglobin. Thus, the ruby and argon laser energy is poorly absorbed by non-pigmented tissue such as the cornea, lens and vitreous humor of the eye, but is preferably absorbed by the pigmented retina where it can then exert a thermal effect.

Another type of laser which has been adapted for surgical use is the carbon dioxide ($CO_2$) gas laser which emits an optical beam which is intensely absorbed by water. The wavelength of the $CO_2$ laser is 10.6 micrometers and therefore lies in the invisible, far infrared region of the electromagnetic spectrum, and is absorbed independently of tissue color by all soft tissues having a high water content. Thus, the $CO_2$ laser makes an excellent surgical scalpel and vaporizer. Since it is completely absorbed, its depth of penetration is shallow and can be precisely controlled with respect to the surface of the tissue being treated. The $CO_2$ laser is thus well adapted for use in various surgical procedures in which it is necessary to vaporize or coagulate neutral tissue with minimal thermal damage to nearby tissues.

Another laser in widespread use is the neodymium doped yttrium-aluminum-garnet (Nd:YAG) laser. The Nd:YAG laser has a predominant mode of operation at a wavelength of 1.064 micrometers in the near infrared region of the electromagnetic spectrum. The Nd:YAG optical emission is absorbed to a greater extent by blood than by water making it useful for coagulating large, bleeding vessels. The Nd:YAG laser at 1,064 micrometers has been transmitted through endoscopes for treatment of a variety of gastrointestinal bleeding lesions, such as esophageal varices, peptic ulcers and arteriovenous anomalies.

Such applications of laser energy are thus well adapted where high energy thermal effects are desired, such as tissue vaporization, tissue cauterization, coagulation and as a surgical scalpel.

The following U.S. patents disclose apparatus and method for therapeutic treatment of living tissue by a laser irradiation:

3,456,651
3,720,213
4,141,362
4,144,888
4,367,729
4,561,440
4,573,465
4,589,404
4,601,288
4,604,992
4,672,969
4,692,924

OBJECT OF THE INVENTION

The application of conventional lasers for the purpose of stimulating soft tissue to cause a reduction in pain and inflammation, in stimulation of microcirculation to reduce healing time has been attempted at very low power levels, typically well under 100 milliwatts. Although some therapeutic benefits have been achieved, the treatment time has been unacceptably long.

Accordingly, the object of the present invention is to provide a method for safely and effectively applying low level reactive laser energy to living tissue for therapeutic purposes, for example, to reduce pain, reduce inflammation and enhance the healing of tissue by stimulation of microcirculation, without exposing the tissue to damaging thermal effects.

SUMMARY OF THE INVENTION

The method of using a low level reactive laser system from 100 milliwatts–800 milliwatts in either a pulsed or continuous mode with optical energy produced by a Nd:YAG laser at a fundamental wavelength of 1064 nanometers has been found to reduce pain in soft tissues, reduce inflammation and enhance the healing of tissue by stimulation of microcirculation without subjecting the living tissue to damaging thermal effects. The living tissue is irradiated with optical energy at a wavelength and at a power dissipation level in the tissue to cause the amount of optical energy absorbed and converted to heat to be within a range bounded by a minimum absorption rate sufficient to elevate the average temperature of the irradiated tissue to a level above the basal body temperature, but which is less than the absorption rate at which tissue is converted into a collagenous substance. The wavelength, spot or beam size, power, time exposure are carefully controlled to produce a noticeable warming effect in the irradiated tissue, but which is limited to avoid tissue damage by thermal effects.

DETAILED DESCRIPTION OF THE PREFERRED METHOD

According to the preferred method, the laser energy is produced by a Nd:YAG laser at a fundamental wavelength of 1064 nanometers at an output power level of from 100–800 milliwatts. The laser optical energy is applied to regions of the body which require a decrease in muscle spasm, increased circulation, decrease in pain or enhanced tissue healing. The surface area is demarcated and the surface of the tissue is irradiated with the laser beam in a grid fashion for the amount of time and intensity necessary to produce the desired therapeutic effect, with the energy density of the irradiated tissue being limited to the range of from about 1 joules/cm$^2$ to about 15 joules/cm$^2$. The intensity and duration of treatment is determined by the character of the tissue to be treated, the depth of penetration desired, the acuteness of the injury and the condition of the patient.

Therapeutic treatment by a low level reactive laser system has been demonstrated for the purposes of reducing pain, reducing inflammation, and enhancing healing of damaged tissue by stimulation of microcirculation, all being successfully accomplished without producing damaging thermal effects in the tissue. A Nd:YAG laser resonator was used as the laser source. Its principal wavelength was 1064 nanometers, and had an adjustable beam energy output of 100 milliwatts–800 milliwatts. The laser was capable of operation in a pulsed or continuous mode, and its output was controlled by an exposure timer in the range of 0.1–9.9 minutes. The pulse on-time was adjustable from 0.1–9.9 seconds in 0.1 second intervals. The pulse off-time was also adjustable from 0.1–9.9 seconds in 0.1 second intervals. The therapeutic beam was directed with a helium-neon laser beam, having an output of less than 1 milliwatt. The Nd:YAG laser beam operates in the near infrared portion of the electromagnetic spectrum at 1.064 microns, and thus is invisible. The visible helium-neon laser beam is in the red portion of the spectrum at 633 nanometers. Both beams are precisely aligned and are coincident upon impact at the tissue site. The method for delivering the beams to the target sight is a flexible quartz fiber and focusing handpiece.

The Nd:YAG laser beam exits the output coupler of the laser head and is steered by a pair of alignment wedges before passing through a circularly variable, neutral density attenuator. Light passing through the attenuator is focused through a pair of 90 mm focal length lenses onto the proximal end of an optical fiber cable.

The main beam attenuator is a shutter placed outside the laser head between the output coupler of the laser and the beam steering mirror. It includes four components: a 90 degree reflecting prism, a shutter arm, a shutter mounting bracket and an actuating solenoid. The prism is mounted to the shutter arm so that, in the normally closed position, the prism intercepts the laser beam and reflects it downwardly into a beam dump in the laser deck. The solenoid is energized when an output channel has been selected and foot pedal is depressed, which causes the shutter arm to raise and allows the beam to pass. When the solenoid arm is de-energized, the shutter drops into the closed position.

A suitable laser system can be obtained from Melles Griot which includes a helium-neon aiming laser, Model 05LHR007 and which includes a Nd:YAG laser, Model 607C.

The optical energy is produced by a source, preferably a laser, having a wavelength of 1064 nanometers in the near infrared region of the electromagnetic spectrum. The laser is provided with an optical fiber guide and coupler for directing the beam of optical energy to the tissue surface. The energy of the optical radiation is controlled and applied to produce a minimum absorption rate in the irradiated tissue which will elevate the average temperature of the irradiated tissue to a level above the basal body temperature, but which does not exceed the maximum absorption rate which is great enough to convert the irradiated tissue into a collagenous substance.

It has been determined through extensive testing that the foregoing condition is satisfied by a Nd:YAG laser operated at its fundamental wavelength of 1064 nanometers at a power output level of from 100–800 milliwatts, with the laser beam being focused to produce an energy density of the projected laser beam in the range of from about 1.0 joule/cm$^2$ to about 15 joules/cm$^2$. Since the laser beam light is coherent, a variable power density of the light was obtained by converging the laser beam into small treatment areas, for example, from about 0.5 mm$^2$ to about 2 mm$^2$ at each grid treatment point.

Certain physiological mechanisms in the tissue and at the cellular level have been observed when the above process is used. In the evaluation of the microcirculatory system, for example, it has been demonstrated the blood vessel walls possess photosensitivity. When the blood vessel walls are exposed to laser irradiation as set forth above, the tonus is inhibited in smooth myoctyes, thus increasing the blood flow in the capillaries. Other effects which have been observed are: peripheral capillarid neovascularization, reduction of blood platelet aggregation, reduction of $O_2$ from the triplet to the singlet form which allows for greater oxygenation of the tissue, reduction of buffer substance concentration in the blood, stabilization of the indices of erythrocyte deformation, reduction of products of perioxidized lipid oxygenation of the blood. Other effects which have been observed are increased index of antithrombin activity, stimulation of the enzymes of the antioxidant system such as superoxide dismutase and catalase. An increase in the venous and lymph and outflow from the irradiated region has been observed. The tissue permeability in the area is substantially enhanced. This assists in the immediate reduction of edema and hematoma concentrations in the tissue. At the cellular level, the mitochondria have also been noted to produce increased amounts of ADP with subsequent increase in ATP. There are also appears to be an increased stimulation of the calcium and sodium pumps at the tissue membrane at the cellular level.

At the neuronal level, the following effects have been observed as a result of the foregoing therapeutic treatment. First, there is an increased action potential of crushed and intact nerves. The blood supply and the number of axons is increased in the irradiated area. Inhibition of scar tissue is noticed when tissue is lazed. There is an immediate increase in the membrane permeability of the nerve. Long term changes in the permeability of calcium and potassium ions through the nerve for at least 120 days have been observed. The RNA and subsequent DNA production is enhanced. Singlet $O_2$ is produced which is an important factor in cell regeneration. Pathological degeneration with nerve injury is changed to regeneration. Both astrocytes and oligodedrocytes are stimulated which causes an increased production of peripheral nerve axons and myelin.

Phagocytosis of the blood cells is increased, thereby substantially reducing infection. There also appears to be a significant anti-inflammatory phenomena which provides a decrease in the inflammation of tendons, nerves, bursae in the joints, while at the same time yielding a strengthening of collagen. There is also an effect on the significant increase of granulation tissue in the closure of open wounds under limited circulation conditions.

Analgesia of the tissue has been observed in connection with a complex series of actions at the tissue level. At the local level, there is a reduction of inflammation, causing a reabsorption of exudates. Enkephalins and endorphins are recruited to modulate the pain production both at the spinal cord level and in the brain. The serotnogenic pathway is also recruited. While it is not completely understood, it is believed that the irradiation of the tissue causes the return of an energy balance at the cellular level which is the reason for the reduction of pain.

Although the invention has been described with reference to preferred method, and with reference to specific therapeutic applications, the foregoing description is not intended to be construed in a limiting sense. Modifications of the disclosed embodiment as well as alternative applications of the invention will be suggested to persons skilled in the art by the foregoing specification. It is therefore contemplated that the appended claims will cover any such modifications or embodiments that fall within the true scope of the invention.

What is claimed is:

1. A method for treating a small treatment area of a biological tissue of a living subject without exposing the tissue to damaging thermal effects, said method comprising:

using a low level reactive laser to generate coherent optical energy radiation having a wavelength in the range of the near infrared region of the electromagnetic spectrum at a power output in the range of from about 100 milliwatts to about 800 milliwatts, and focusing said coherent optical energy radiation on said small treatment area to achieve a rate of absorption and conversion to heat in the irradiated tissue in the range between a minimum rate, sufficient to elevate the average temperature of the irradiated tissue to a level above the basal body temperature of the living subject, and a maximum rate which is less than the rate at which the irradiated tissue is converted into a collagenous substance.

2. A method in accordance with claim 1 wherein said wavelength is about 1064 nanometers.

3. A method in accordance with claim 2 wherein said low level reactive laser comprises a Nd:YAG laser.

4. A method in accordance with claim 3 wherein said tissue is irradiated with said coherent optical energy radiation at a plurality of small treatment areas in a grid for the amount of time and intensity necessary to provide a therapeutic effect.

5. A method in accordance with claim 3 wherein each small treatment area has an area in the range of about 0.5 mm$^2$ to about 2 mm$^2$.

6. A method in accordance with claim 3 wherein said low level reactive laser is pulsed with each pulse on time being in the range of 0.1 to 9.9 seconds and each pulse off time being in the range of 0.1 to 9.9 seconds.

7. A method in accordance with claim 3 wherein said low level reactive laser is operated in a continuous mode.

8. A method in accordance with claim 1 wherein said low level reactive laser comprises a Nd:YAG laser.

9. A method in accordance with claim 1 wherein said tissue is irradiated with said coherent optical energy radiation at a plurality of treatment points in a grid for the amount of time and intensity necessary to provide a therapeutic effect.

10. A method in accordance with claim 1 wherein each treatment point had an area in the range of about 0.5 mm$^2$ to about 2 mm$^2$.

11. A method in accordance with claim 1 wherein said low level reactive laser is pulsed with each pulse on time being in the range of 0.1 to 9.9 seconds and each pulse off time being in the range of 0.1 to 9.9 seconds.

12. A method in accordance with claim 1 wherein said low level reactive laser is operated in a continuous mode.

* * * * *

UNITED STATES PATENT AND TRADEMARK OFFICE
CERTIFICATE OF CORRECTION

PATENT NO.       : 5,445,146
APPLICATION NO.  : 07/724335
DATED            : August 29, 1995
INVENTOR(S)      : Gary J. Bellinger It is certified that error appears in the above-identified patent and that said Letters Patent is hereby corrected as shown below:

Column 6, Lines 28 – 29:

After "collagenous substance" please insert -- , wherein the density of the optical energy radiation is in the range of from about 1.0 joule/cm$^2$ to about 15 joule/cm$^2$ at the irradiated tissue site. --

Signed and Sealed this

Eleventh Day of May, 2010

David J. Kappos
*Director of the United States Patent and Trademark Office*